US006709454B1

(12) United States Patent
Cox et al.

(10) Patent No.: US 6,709,454 B1
(45) Date of Patent: Mar. 23, 2004

(54) SELF-EXPANDING STENT WITH ENHANCED DELIVERY PRECISION AND STENT DELIVERY SYSTEM

(75) Inventors: Daniel L. Cox, Palo Alto, CA (US); William James Harrison, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/495,395

(22) Filed: Jan. 31, 2000

Related U.S. Application Data

(63) Continuation-in-part of application No. 09/313,780, filed on May 17, 1999.

(51) Int. Cl.⁷ .................................................. A61F 2/06
(52) U.S. Cl. ........................................ 623/1.16; 623/1.2
(58) Field of Search .................................. 623/1.16, 1.2

(56) References Cited

U.S. PATENT DOCUMENTS

| | | |
|---|---|---|
| 3,868,956 A | 3/1975 | Alfidi et al. |
| 4,300,244 A | 11/1981 | Bokros |
| 4,323,071 A | 4/1982 | Simpson et al. |
| 4,332,254 A | 6/1982 | Lundquist |
| 4,439,185 A | 3/1984 | Lundquist |
| 4,468,224 A | 8/1984 | Enzmann et al. |
| 4,512,338 A | 4/1985 | Balko et al. |
| 4,516,972 A | 5/1985 | Samson |
| 4,538,622 A | 9/1985 | Samson et al. |
| 4,554,929 A | 11/1985 | Samson et al. |
| 4,569,347 A | 2/1986 | Frisbie |
| 4,571,240 A | 2/1986 | Samson et al. |
| 4,580,568 A | 4/1986 | Gianturco |
| 4,616,652 A | 10/1986 | Simpson |
| 4,655,771 A | 4/1987 | Wallsten |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,762,128 A | 8/1988 | Rosenbluth |
| 4,790,315 A | 12/1988 | Mueller, Jr. et al. |
| 4,795,458 A | 1/1989 | Regan |
| 4,800,882 A | 1/1989 | Gianturco |
| 4,830,003 A | 5/1989 | Wolff et al. |
| 4,878,906 A | 11/1989 | Lindemann et al. |
| 4,886,062 A | 12/1989 | Wiktor |
| 4,893,623 A | 1/1990 | Rosenbluth |
| 4,907,336 A | 3/1990 | Gianturco |
| 4,913,141 A | 4/1990 | Hillstead |

(List continued on next page.)

FOREIGN PATENT DOCUMENTS

| | | | |
|---|---|---|---|
| EP | 0 556 940 A1 | 8/1993 | |
| FR | 2781143 A1 * | 1/2000 | ........... A61F/02/06 |
| WO | WO 95/33422 | 12/1995 | |
| WO | WO 96/39998 | 12/1996 | |
| WO | WO 98/22159 | 5/1998 | |
| WO | WO 98/53759 | 12/1998 | |

OTHER PUBLICATIONS

Michael J. Wallace, et al.; "Tracheobronchial Tree: Expandable Metallic Stents Used in Experimental and Clinical Applications", Radiology, Feb., 1986, pp. 309–312.

"Coronary Wallstent Endoprosthesis", Schneider Innovation for Life, Schneider (Europe), Switzerland, 1986, 4 pages.

*Primary Examiner*—Corrine McDermott
*Assistant Examiner*—Choon Koh
(74) *Attorney, Agent, or Firm*—Fulwider Patton Lee & Utecht, LLP

(57) ABSTRACT

A self-expanding stent for implantation into a body lumen, such as an artery, includes a plurality of radially expandable cylindrical elements generally aligned on a common longitudinal stent axis and interconnected by a plurality of interconnecting members placed on the stent in a collinear arrangement such as to create at least one continuous spine which extends along the length of the stent. The stent has cylindrical elements at each end of the stent which includes a plurality of double curved portions.

23 Claims, 10 Drawing Sheets

U.S. PATENT DOCUMENTS

| | | |
|---|---|---|
| 4,950,227 A | 8/1990 | Savin et al. |
| 4,969,458 A | 11/1990 | Wiktor |
| 4,969,890 A | 11/1990 | Sugita et al. |
| 4,990,155 A | 2/1991 | Wilkoff |
| 4,998,539 A | 3/1991 | Delsanti |
| 5,002,560 A | 3/1991 | Machold et al. |
| 5,026,377 A | 6/1991 | Burton et al. |
| 5,034,001 A | 7/1991 | Garrison et al. |
| 5,035,706 A | 7/1991 | Giantureo et al. |
| 5,037,392 A | 8/1991 | Hillstead |
| 5,037,427 A | 8/1991 | Harada et al. |
| 5,041,126 A | 8/1991 | Gianturco |
| 5,059,166 A | 10/1991 | Fischell et al. |
| 5,061,275 A | 10/1991 | Wallsten et al. |
| 5,064,435 A | 11/1991 | Porter |
| 5,071,407 A | 12/1991 | Termin et al. |
| 5,078,720 A | 1/1992 | Burton et al. |
| 5,089,005 A | 2/1992 | Harada |
| 5,089,006 A | 2/1992 | Stiles |
| 5,092,877 A | 3/1992 | Pinchuk |
| 5,102,417 A | 4/1992 | Palmaz |
| 5,108,416 A | 4/1992 | Ryan et al. |
| 5,123,917 A | 6/1992 | Lee |
| 5,133,732 A | 7/1992 | Wiktor |
| 5,135,517 A | 8/1992 | McCoy |
| 5,137,513 A | 8/1992 | McInnes et al. |
| 5,158,548 A | 10/1992 | Lau et al. |
| 5,163,952 A | 11/1992 | Froix |
| 5,163,958 A | 11/1992 | Pinchuk |
| 5,171,262 A | 12/1992 | MacGregor |
| 5,183,085 A | 2/1993 | Timmermans |
| 5,192,297 A | 3/1993 | Hull |
| 5,197,978 A | 3/1993 | Hess |
| 5,222,964 A | 6/1993 | Cooper |
| 5,222,969 A | 6/1993 | Gillis |
| 5,222,971 A | 6/1993 | Willard et al. |
| 5,226,913 A | 7/1993 | Pinchuk |
| 5,242,451 A | 9/1993 | Harada et al. |
| 5,256,146 A | 10/1993 | Ensminger et al. |
| 5,258,020 A | 11/1993 | Froix |
| 5,263,964 A | 11/1993 | Purdy |
| 5,282,823 A | 2/1994 | Schwartz et al. |
| 5,282,824 A | 2/1994 | Gianturco |
| 5,300,085 A | 4/1994 | Yock |
| 5,304,200 A | 4/1994 | Spaulding |
| 5,306,294 A | 4/1994 | Winston et al. |
| 5,330,500 A | 7/1994 | Song |
| 5,354,308 A | 10/1994 | Simon et al. |
| 5,354,309 A | 10/1994 | Schnepp-Pesch et al. |
| 5,356,423 A | 10/1994 | Tihon et al. |
| 5,372,600 A | 12/1994 | Beyar et al. |
| 5,378,239 A | | 1/1995 | Termin et al. |
| 5,391,172 A | | 2/1995 | Williams et al. |
| 5,395,390 A | | 3/1995 | Simon et al. |
| 5,403,341 A | | 4/1995 | Solar |
| 5,405,377 A | | 4/1995 | Cragg |
| 5,411,507 A | | 5/1995 | Heckele |
| 5,415,664 A | | 5/1995 | Pinchuk |
| 5,421,955 A | | 6/1995 | Lau et al. |
| 5,433,496 A | * | 7/1995 | Schwartz et al. |
| 5,447,503 A | * | 9/1995 | Miller |
| 5,449,373 A | * | 9/1995 | Pinchasik et al. |
| 5,453,090 A | * | 9/1995 | Martinez et al. |
| 5,456,694 A | * | 10/1995 | Marin et al. |
| 5,458,615 A | * | 10/1995 | Klemm et al. |
| 5,478,349 A | * | 12/1995 | Nicholas |
| 5,484,444 A | * | 1/1996 | Braunschweiler et al. |
| 5,496,277 A | * | 3/1996 | Termin et al. |
| 5,496,346 A | * | 3/1996 | Horzewski et al. |
| 5,507,767 A | * | 4/1996 | Maeda et al. |
| 5,514,154 A | * | 5/1996 | Lau et al. |
| 5,522,883 A | * | 6/1996 | Slater et al. |
| 5,534,007 A | * | 7/1996 | St. Germain et al. |
| 5,554,181 A | * | 9/1996 | Das |
| 5,569,295 A | | 10/1996 | Lam |
| 5,571,135 A | | 11/1996 | Fraser et al. |
| 5,571,168 A | | 11/1996 | Toro |
| 5,603,721 A | | 2/1997 | Lau et al. |
| 5,626,600 A | | 5/1997 | Horzewski et al. |
| 5,634,928 A | | 6/1997 | Fischell et al. |
| 5,653,727 A | | 8/1997 | Wiktor |
| 5,728,158 A | * | 3/1998 | Lau et al. ............... 623/1.16 |
| 5,755,777 A | | 5/1998 | Chuter |
| 5,759,192 A | | 6/1998 | Saunders |
| 5,788,707 A | | 8/1998 | Del Toro et al. |
| 5,827,321 A | | 10/1998 | Roubin et al. |
| 5,836,965 A | | 11/1998 | Jendersee et al. |
| 5,843,117 A | | 12/1998 | Alt et al. |
| 5,888,201 A | | 3/1999 | Stinson et al. |
| 5,910,145 A | * | 6/1999 | Fischell et al. |
| 5,925,061 A | * | 7/1999 | Ogi et al. |
| 5,931,867 A | * | 8/1999 | Haindl |
| 5,944,726 A | * | 8/1999 | Blaeser et al. |
| 5,954,764 A | * | 9/1999 | Parodi |
| 5,968,069 A | * | 10/1999 | Dusbabek et al. |
| 5,980,533 A | * | 11/1999 | Holman |
| 5,989,280 A | * | 11/1999 | Euteneuer et al. |
| 6,001,123 A | * | 12/1999 | Lau |
| 6,019,778 A | * | 2/2000 | Wilson et al. |
| 6,051,021 A | | 4/2000 | Frid |
| 6,059,810 A | | 5/2000 | Brown et al. |
| 6,086,610 A | | 7/2000 | Duerig et al. |

\* cited by examiner

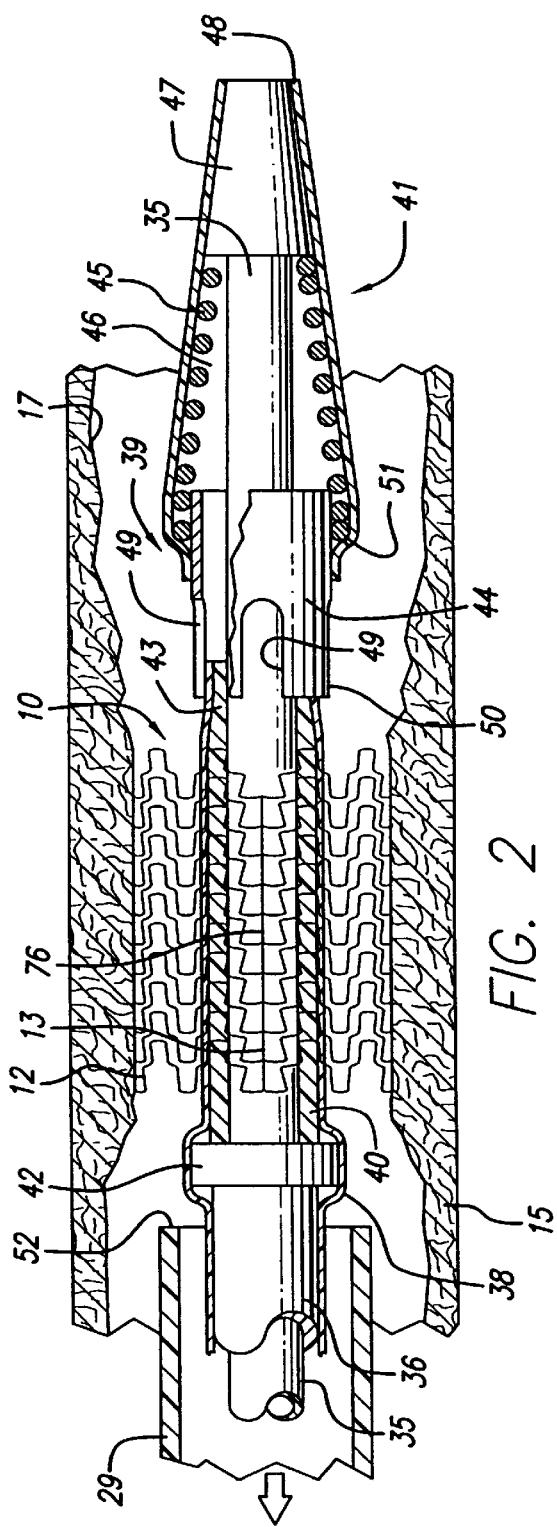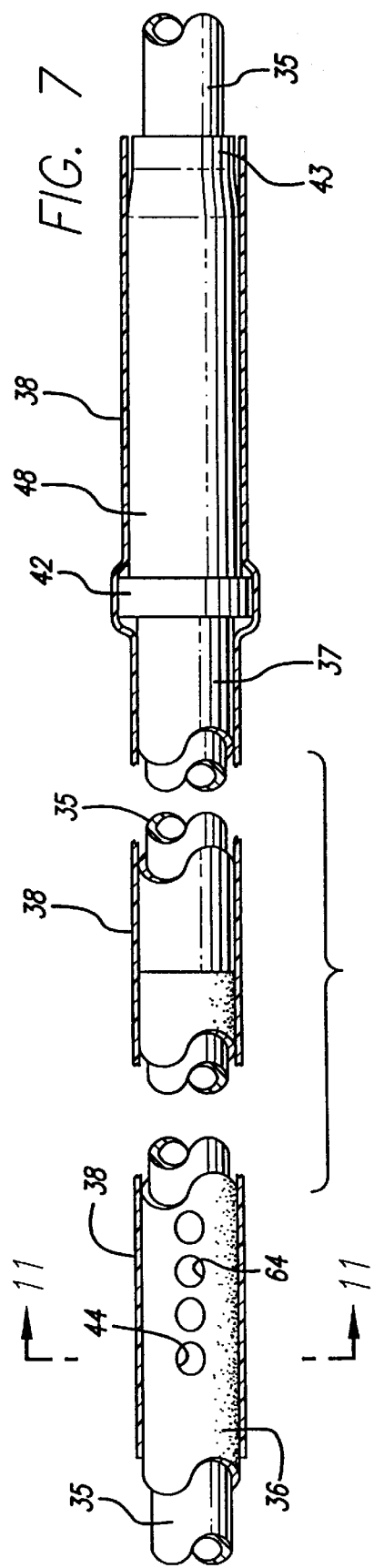

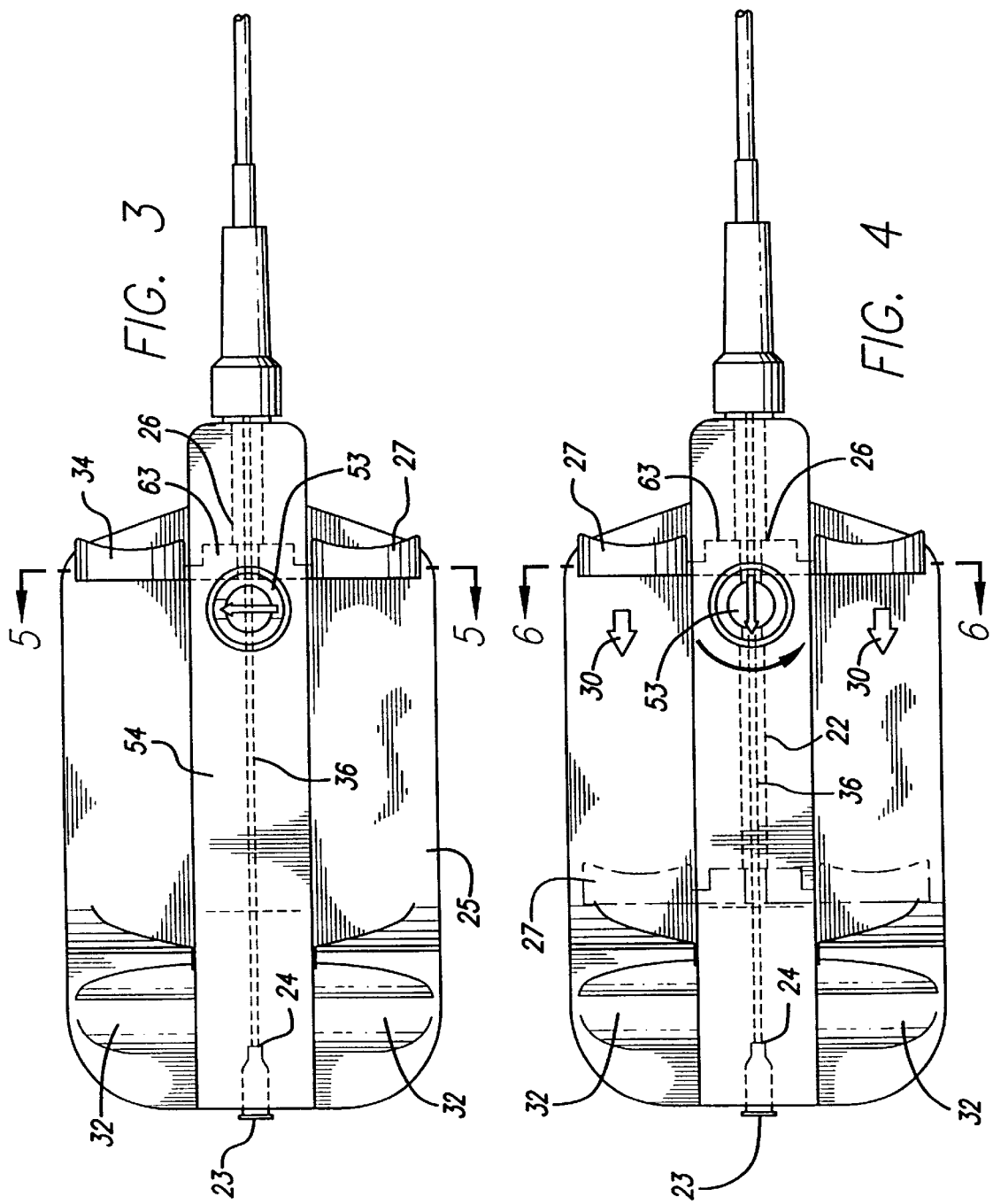

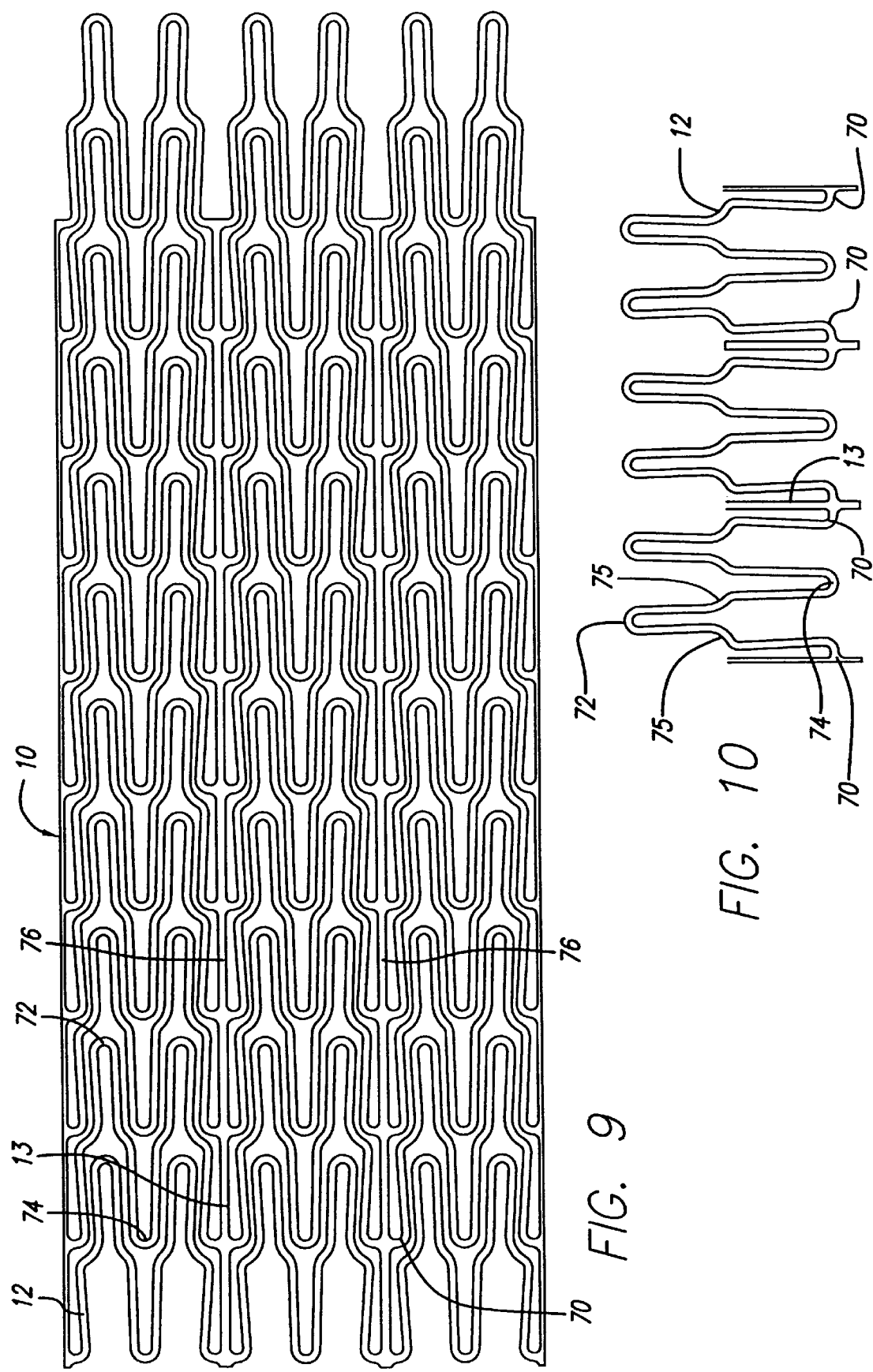

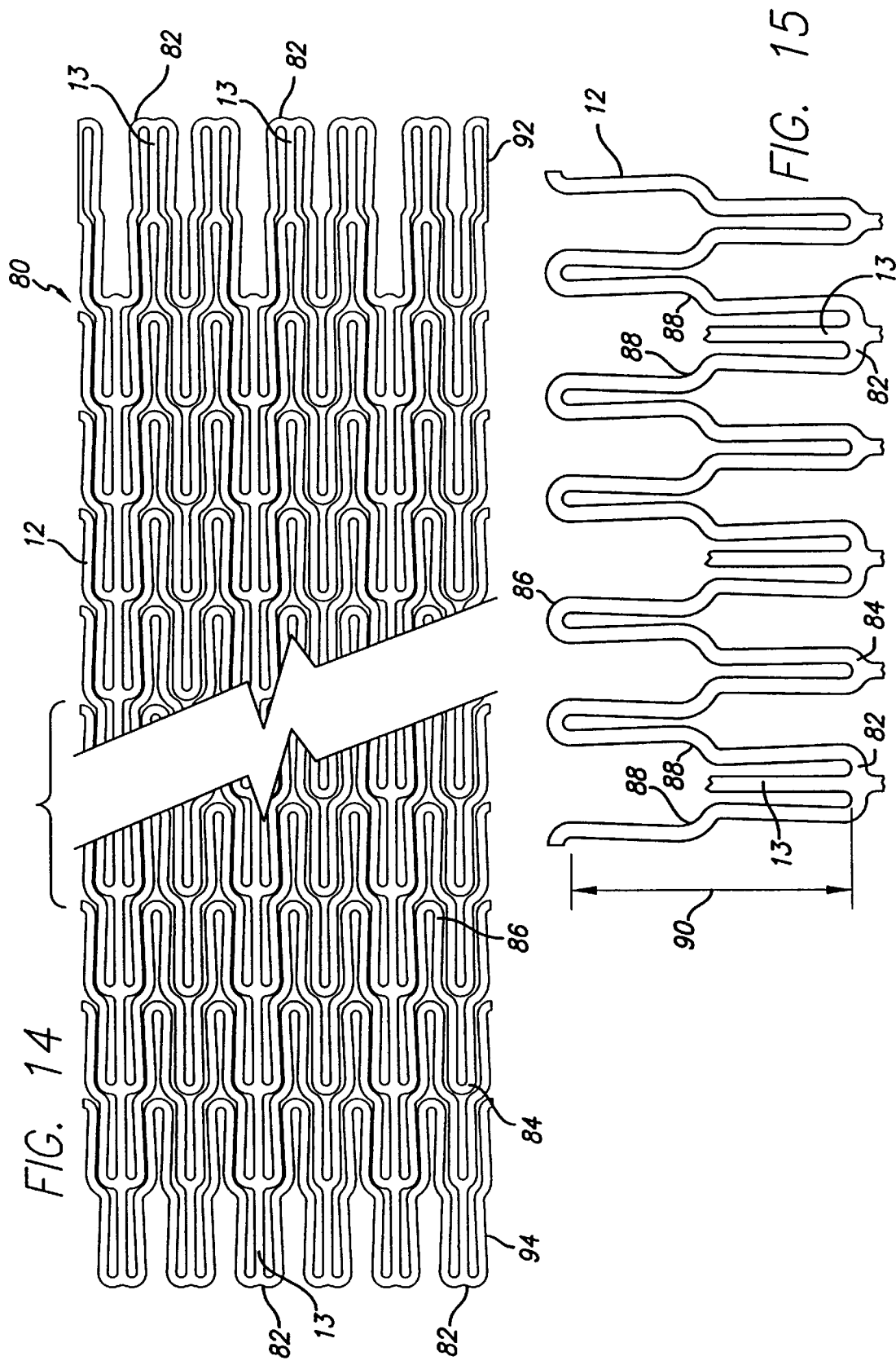

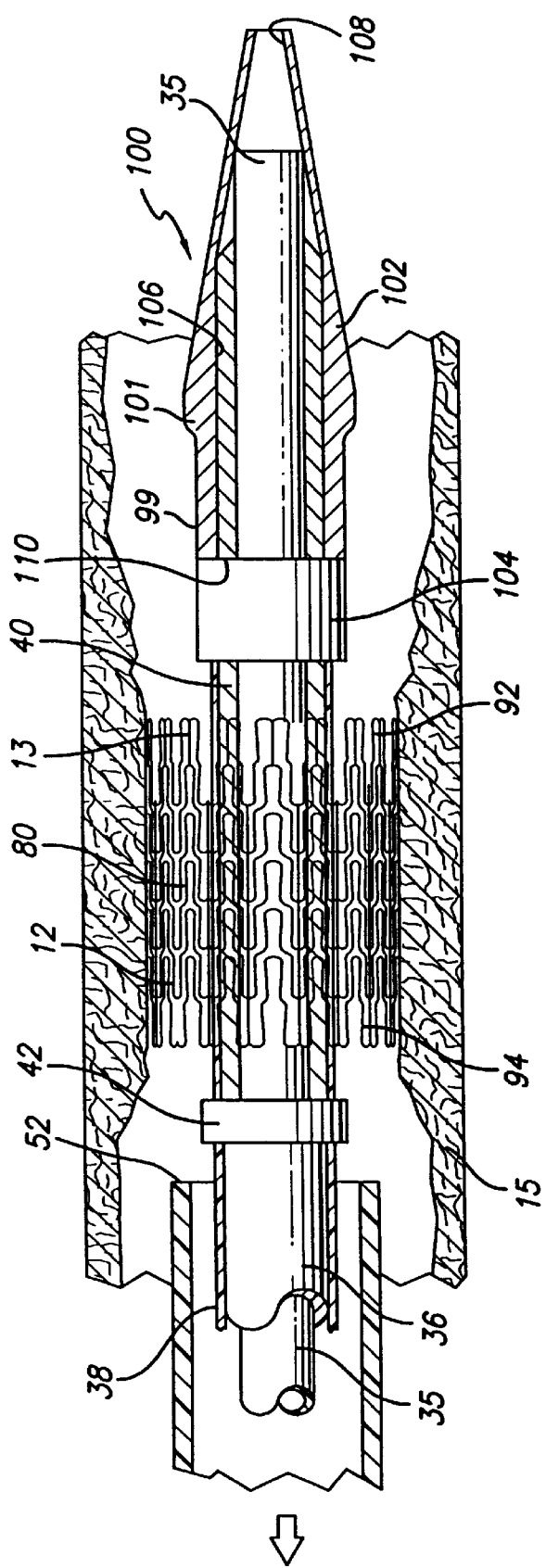
FIG. 18
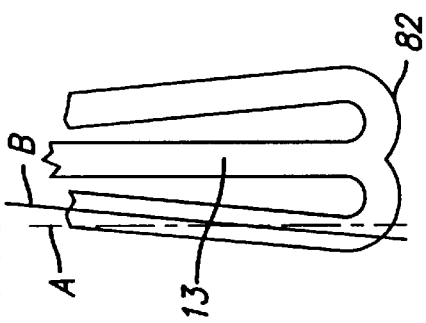
FIG. 17
FIG. 16

SELF-EXPANDING STENT WITH ENHANCED DELIVERY PRECISION AND STENT DELIVERY SYSTEM

This application is a continuation-in-part of application Ser. No. 09/313,780 filed on May 17, 1999, which is assigned to the same Assignee as the present application.

BACKGROUND OF THE INVENTION

The present invention relates to expandable endoprosthesis devices, generally called stents, which are adapted to be implanted into a patient's body lumen, such as a blood vessel, to maintain the patency thereof, along with systems for delivering and deploying such stents. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis.

Stents are generally cylindrically shaped devices which function to hold open and sometimes expand a segment of a blood vessel or other arterial lumen, such as a coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a compressed state when the stent is advanced out of the distal end of the delivery catheter into the blood vessel. Such stents manufactured from expandable heat sensitive materials allow for phase transformations of the material to occur, resulting in the expansion and contraction of the stent. Other stents include those made with a branded configuration that does not go through plastic deformation.

Details of prior art expandable stents can be found in U.S. Pat. No. 3,868,956 (Alfidi et al.); U.S. Pat. No. 4,512,1338 (Balko et al.); U.S. Pat. No. 4,553,545 (Maass, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallsten); U.S. Pat. No. 4,739,762 (Palmaz); and U.S. Pat. No. 5,569,295 (Lam), which are hereby incorporated by reference.

Further details of prior art self-expanding stents can be found in U.S. Pat. No. 4,580,568 (Gianturco); and U.S. Pat. No. 4,830,003 (Wolff, et al.), which are hereby incorporated by reference.

Some prior art stent delivery systems for implanting self-expanding stents include an inner lumen upon which the compressed or collapsed stent is mounted and an outer restraining sheath which is initially placed over the compressed stent prior to deployment. When the stent is to be deployed in the body vessel, the outer sheath is moved in relation to the inner lumen to "uncover" the compressed stent, allowing the stent to move to its expanded condition. Some delivery systems utilize a "push-pull" type technique in which the outer sheath is retracted while the inner lumen is pushed forward. Still other systems use an actuating wire which is attached to the outer sheath. When the actuating wire is pulled to retract the outer sheath and deploy the stent, the inner lumen must remain stationary, preventing the stent from moving axially within the body vessel.

However, problems have been associated with prior art delivery systems. For example, systems which rely on a "push-pull design" can experience movement of the collapsed stent within the body vessel when the inner lumen is pushed forward which can lead to inaccurate positioning and, in some instances, possible perforation of the vessel wall by a protruding end of the stent. Systems which utilize an actuating wire design will tend to move to follow the radius of curvature when placed in curved anatomy of the patient. As the wire is actuated, tension in the delivery system can cause the system to straighten. As the system straightens, the position of the stent changes because the length of the catheter no longer conforms to the curvature of the anatomy. This change of the geometry of the system within the anatomy can also lead to inaccurate stent positioning.

Another difficulty which can be encountered with some existing self-expanding stents is the fact that the length of the stent can shorten dramatically during deployment, making it difficult to precisely position the stent within the artery. Since proper positioning of the stent is critical to the performance of the stent, it is imperative that the physician know the exact length and diameter that the stent will expand to upon deployment. A self-expanding stent which shortens in length upon radial expansion of the device can cause problems to the physician attempting to accurately position the stent within the target site. Additionally, some existing self-expanding stents can store energy axially as the outer restraining sheath is retracted. Frictional force generated as the outer sheath is retracted over the self-expanding stent can cause the stent to act somewhat like a spring, storing energy as the frictional force acts on the stent. The stored energy is released as the stent expands beyond the end of the sheath, and this release of energy can cause the stent to move or "jump" from the desired position, resulting in inaccurate placement. The amount of energy stored is dependent on the flexibility of the stent and the friction between the stent and the outer sheath.

The above-described stent delivery systems also can be somewhat difficult to operate with just one hand, unless a mechanical advantage system (such as a gear mechanism) is utilized. Often, deployment with one hand is desirable since it allows the physician to use his/her other hand to support a guiding catheter which is also utilized during the procedure, allowing the physician to prevent the guiding catheter from moving during deployment of the stent. Neither of the above-described prior art stent delivery systems prevents any axial movement of the catheters of the system during stent deployment. Even a slight axial movement of the catheter assembly during deployment can cause inaccurate placement of the stent in the body lumen.

What has been needed and heretofore unavailable is a self-expanding stent which has a high degree of flexibility so that it can be advanced through tortuous passageways of the anatomy and can be expanded up to its maximum diameter with minimal, or no longitudinal contraction, and yet have sufficient mechanical strength to hold the body lumen open. The self-expanding stent should also store little or no energy during sheath retraction to prevent "jumping" of the stent from occurring to allow for more accurate positioning within the body lumen. Also, there is a need for a stent delivery system which facilitates minimal movement during stent deployment, provides accurate stent placement, and provides single handed operation by the physician. The present inventions disclosed herein satisfy all of these needs.

SUMMARY OF THE INVENTION

The present invention is directed to a self-expanding stent having a configuration which permits the stent to be expanded radially to larger diameters while preventing longitudinal shortening of the stent during expansion. As a result, the present invention provides a stent which maintains a constant length from its fully compressed condition all the way through to its fully expanded condition. A self-expanding stent made in accordance with the present invention provides for more accurate placement during the delivery of the stent to the target site in the body lumen. The stent remains relatively flexible along its longitudinal axis in order to facilitate delivery through tortuous body lumens, but is strong enough radially in its expanded condition to maintain the patency of the body lumen, such as an artery or other vessel, when implanted therein.

The stent of the present invention also minimizes the potential for storing energy as the outer restraining sheath of the stent delivery catheter is retracted over the compressed stent. The structure of the stent made in accordance with the present invention stores little or no energy during deployment, reducing the likelihood that the stent will "jump" off of the delivery catheter during deployment. As a result, a smooth and controlled deployment can be achieved when utilizing the stent of the present invention. This stent design results in a low profile device which maintains good flexibility to reach even distal lesions.

The stent of the present invention includes a plurality of adjacent cylindrical elements (also referred to as "rings") which are independently expandable in the radial direction and arranged along a common longitudinal axis. The cylindrical elements are formed in an irregular serpentine wave pattern transverse to the longitudinal axis and continuing in a plurality of alternating peaks and valleys. Each cylindrical element is connected to an adjacent cylindrical element by at least one interconnecting member which is aligned longitudinally with another interconnecting member to create a continuous spine which runs the length of the stent to prevent any significant stent shortening during expansion. The continuous spine also helps prevent unwanted storage of energy in the stent as the outer restraining sheath of the delivery catheter is retracted to deploy the stent.

In one embodiment of the present invention, each cylindrical element is connected to an adjacent cylindrical element by three interconnecting members which are circumferentially positioned 120 degrees apart. In this embodiment, the interconnecting members are aligned to form three continuous spines along the length of the stent, again to prevent any significant shortening of the stent during radial expansion and to prevent unwanted storage of energy as the outer restraining sheath is retracted for deployment.

One preferred structure for the expandable cylindrical elements which form the stent of the present invention generally has a circumferential serpentine pattern along a plurality of alternating peaks and valleys. Each cylindrical element contains three (3) (W) and three (3) (U) shaped patterns which form the valleys of the stent. Each (W) and (U) shaped valley is connected by an (inverted U) shaped pattern which forms the peaks of the cylindrical element. As the stent expands, the (W), and (U) and inverted (inverted U) patterns open circumferentially, with the interconnecting members maintaining the spacing between each cylindrical element. To minimize the gaps between the struts when the stent is expanding, each serpentine cylindrical element is designed to extend into the space between the (W), the (U) and the (inverted U) of an adjacent cylindrical element. The interconnecting members ensure minimal longitudinal contraction during radial expansion of the stent in the body vessel. Preferably the serpentine patterns have varying degrees of curvature in the regions of the peaks and valleys and are adapted so that radial expansion of the cylindrical elements are generally uniform around their circumferences during expansion of the stent from the contracted condition to the expanded condition.

The resulting stent structure is a series of radially expandable cylindrical elements that are spaced longitudinally close enough so that small dissections in the wall of a body lumen may be pressed back into position against the luminal wall, yet does not compromise the longitudinal flexibility of the stent both when being negotiated through the body lumens in the unexpanded state and when expanded into position. The serpentine patterns allow for even expansion around the circumference by accounting for the relative differences in stress created by the radial expansion of the cylindrical elements. Each of the individual cylindrical elements may rotate slightly relative to their adjacent cylindrical elements without significant deformation, cumulatively providing a stent which is flexible along its length and longitudinal axis, but which is still very stable in the radial direction in order to resist collapse after expansion.

The stent of the present invention can be laser cut from a tube of super elastic nickel-titanium (Nitinol) whose transformation temperature is below body temperature. All of the stent diameters are cut with the same stent pattern, and the stent is expanded and heat treated to be stable at the desired final diameter. The heat treatment also controls the transformation temperature of the Nitinol such that the stent is super elastic at or below body temperature. The stent is electro-polished to obtain a smooth finish with a thin layer of titanium oxide placed on the surface. The stent is usually implanted into the target vessel which is smaller than the stent diameter so that the stent applies a force to the vessel wall to keep it open.

After the stent is expanded, some of the peaks and/or valleys may, but not necessarily, tip outwardly and embed in the vessel wall. Thus, after expansion, the stent might not have a smooth outer wall surface. Rather, they might have small projections which embed in the vessel wall and aid in retaining the stent in place in the vessel.

The elongated interconnecting members which interconnect adjacent cylindrical elements should have a transverse cross-section similar to the transverse dimensions of the undulating components of the expandable cylindrical elements. The interconnecting members may be formed in a unitary structure with the expandable cylindrical elements formed from the same intermediate product. The stent could also be made from a sheet of material with the pattern of the cylindrical elements and interconnecting elements cut by a laser. The sheet could then be formed into a cylinder by welding a longitudinal seam using laser welding or other known techniques.

Preferably, the number and location of the interconnecting members can be varied in order to develop the desired longitudinal flexibility provided by the rings in the stent structure both in the compressed condition as well as in the expanded condition. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels. The number of spines formed by the collinear arrangement of interconnecting elements can vary from one to as many as can be reasonably placed on the stent, however, for minimal energy storage with maximum flexibility, two to four spines are preferred.

The stent of the present invention is particularly useful for implantation in body lumens which are located along the outer portions of the body where external forces could possibly be applied to the stent. For example, the stent of the present invention is particularly advantageous for implantation in the carotid arteries which are susceptible to external forces. Since the Nitinol stent is crush resistant, it will spring back to its original expanded condition even after an external force is applied to it. As a result, there is less likelihood that the stent would be deformed or crushed by an external force. Additionally, due to the springy and softer composition of the stent, there is less likelihood that the struts of the stent would cut into the underlying plaque build-up upon application of a force which may otherwise create small pieces of plaque that would enter the bloodstream.

Another embodiment of the present invention enables the stent to expand to a larger maximum size and collapse to a smaller size. The stent also has increased axial rigidity through the use of additional interconnecting members at the outermost cylindrical elements which not only increases the end strength of the stent, but may also provide additional radiopacity to the device. In this embodiment, the (W), (U) and (inverted U) portions of each cylindrical element are modified somewhat so that each arc angle "wraps" more than 180 degrees, providing a smaller collapsed capacity, yet has the same size strut width. This particular embodiment of the present invention also utilizes a number of spines formed by a collinear arrangement of interconnecting elements. The number of spines can vary from one to as many as can be reasonably placed on the stent, however, for minimum energy storage with maximum flexibility, two to four spines are preferred.

The present invention also is directed to a stent delivery system which can be used to provide accurate deployment of a self-expanding stent into a target site in a patient's body lumen. The stent delivery system in accordance with the present invention incorporates unique features which facilitate minimal movement during stent deployment, accurate stent placement, and single-handed system operation. The stent delivery system can be used to deploy the novel self-expanding stent disclosed herein, or any self-expanding stent.

One embodiment of a stent delivery system made in accordance with the present invention includes an elongated catheter body having a proximal and distal end. The elongated catheter body is made up of an inner tubular member which extends within an outer tubular member in a coaxial arrangement. The outer tubular member has a restraining sheath at its distal end which holds the stent, which is mounted on the inner tubular member, in its compressed delivery position until ready for deployment. The outer tubular member and restraining sheath are retractable to release the compressed stent to its expanded condition. The proximal ends of the inner and outer tubular members are connected to a housing assembly which provides a manual mechanism for retracting the restraining sheath and immobilizing the inner tubular member, preventing it from moving relative to the restraining sheath during stent deployment. The proximal end of the outer tubular member is attached to a pull-back handle located on the housing assembly which is moved by the physician in order to retract the restraining sheath and deploy the compressed stent. A luer fitting attached to the proximal end of the inner tubular member is rigidly fixed to the housing base to prevent the inner tubular member from moving when the outer tubular member is retracted.

The inner tubular member has a guide wire lumen which extends from the distal end of the inner tubular member to the proximal end to allow a guide wire to be used to advance the elongated catheter body to the target area in the body lumen in an "over the wire" technique. In this regard, the catheter stent assembly can be introduced within the patient's vasculature in a conventional Seldinger technique through a guiding catheter. The distal end of the inner tubular member includes a soft, low profile tip assembly with a radiopaque marker. An additional radiopaque marker is placed proximal to the collapsed stent.

In one embodiment of the present invention, the inner tubular member is made with three (3) coaxial layers of materials. The inner most layer is the guide wire lumen (described above) which runs the entire length of the catheter body. A second layer of the inner tubular member is composed of a proximal portion made from stainless steel hypotube and a distal reinforcing portion which can be made from a material with high compressive strength such as polyetheretherketone (PEEK). The outermost part of the inner tubular member is a thin layer shrink tubing.

In another embodiment, the tip assembly of the inner tubular member includes a tubular element made from a piece of stainless steel hypotube to which a wound coil is welded. The coil and the distal end of the tubular element are encased in molded urethane. The distal end of the urethane body is loaded with radiopaque tungsten making the tip assembly radiopaque. The proximal end of the tubular segment can include circumferential slots which are cut into the proximal end to provide a channel which allows air and fluid to escape when the catheter assembly is flushed to evacuate air from the system.

The housing assembly of the stent delivery system is designed so that the operator retracts only the outer restraining sheath while the inner tubular member remain stationary. Due to the unique design of the housing assembly, the physician pushes down on the housing assembly during deployment and not forward. This prevents the inner tubular member assembly from moving forward toward the patient. The housing assembly includes a uniquely curved base which has a contour which conforms to the patient's leg. The design of the housing allows the system to be operated by just one hand, freeing the physician's other hand for other purposes, such as stabilizing the guiding catheter during stent deployment.

The stent delivery system of the present invention also includes a unique flushing system which is used to evacuate air from the system. The flushing system consists of small openings extending through the inner tubular member near the end of the proximal portion of the inner member. The openings are drilled through the guide wire lumen to effectively open up a passageway from the guide wire lumen to the annular space formed between the inner tubular member and the outer tubular member. A syringe is attached to the luer fitting at the housing assembly and sterile fluid is pumped into the guide wire lumen in order to flush air from the system. A mandrel placed in the guide wire lumen at the tip assembly blocks the flow of the sterile fluid through the distal tip. The sterile fluid is thus forced to flow out of the small openings into the annular space formed between the inner tubular member and outer tubular member. The fluid flows past the collapsed stent where the fluid will eventually escape either through the small circumferential slots cut into the tubular element of the tip assembly or from the sheath directly. Once fluid is observed dripping from the end of the restraining sheath, the mandrel can be removed since air has been evacuated from the system. Since the gap sizes are so small between the various components, capillary force prevents air from infiltrating the delivery system once the evacuation has been completed.

These and other advantages of the present invention become apparent from the following detailed description and the accompanying exemplary drawings.

BRIEF DESCRIPTION OF THE DRAWINGS

FIG. 2 is an elevational view, partially in section, similarly to that shown in FIG. 1, wherein the stent is expanded within the vessel.

FIG. 3 is a plan view showing the housing assembly of the stent delivery system shown in FIG. 1 in its locked position.

FIG. 4 is a plan view of the housing assembly of the stent delivery system shown in FIG. 1 in its unlocked position.

FIG. 7 is an elevational view of the inner tubular member of the catheter portion of the stent delivery system made in accordance with the present invention.

FIG. 9 is a plan view of a preferred embodiment of a flattened section of a stent of the present invention, which illustrates the serpentine pattern with the interconnecting members arranged collinearly to form a continuous spine along the stent.

FIG. 10 is an enlarged partial view of the stent of FIG. 9 depicting the serpentine pattern along the peaks and valleys which form the cylindrical element of the stent of the present invention.

FIG. 14 is a plan view of a flattened section of a stent of the present invention which illustrates the undulating pattern on the stent shown in FIG. 13.

FIG. 15 is an enlarged view of one cylindrical element of the stent of FIGS. 13 and 14 depicting the serpentine pattern with the peaks and valleys made in accordance with the present invention.

FIG. 16 is an enlarged view of one of the peak portions (inverted U) of a cylindrical element of the present invention which shows the slight inward angulation of the legs of this element.

FIG. 17 is an enlarged view of one of the double curved portions (W) of a cylindrical element of the present invention which shows the slight inward angulation of the outer legs of this element.

FIG. 18 is an elevational view, partially in section, depicting the self-expanding stent embodying features of the present invention as it is expanded within a body vessel along with an alternative embodiment of the tip assembly of the stent delivery system which is made in accordance with the present invention.

DETAILED DESCRIPTION OF THE PREFERRED EMBODIMENTS

The present invention is directed to a self-expanding stent with enhanced delivery precision and a stent delivery system for accurately placing self-expanding stents into a target site in a body lumen. While the present invention is described in detail as applied to the coronary arteries of a patient, those skilled in the art will appreciate it that it can also be used in other body lumens as well, peripheral arteries such as the carotid artery, and veins.

FIGS. 1–4 illustrate a self-expanding stent 10 incorporating features of the present invention. The stent 10 is mounted onto a stent delivery system 11 which is also made in accordance with the present invention. The stent 10 generally comprises a plurality of radially expandable cylindrical elements 12 disposed generally coaxially and connected by interconnecting members 13 disposed between adjacent cylindrical elements 12. Additional details regarding the particular structure and shape of the various elements making up the stent 10 are provided below.

Figure 1:
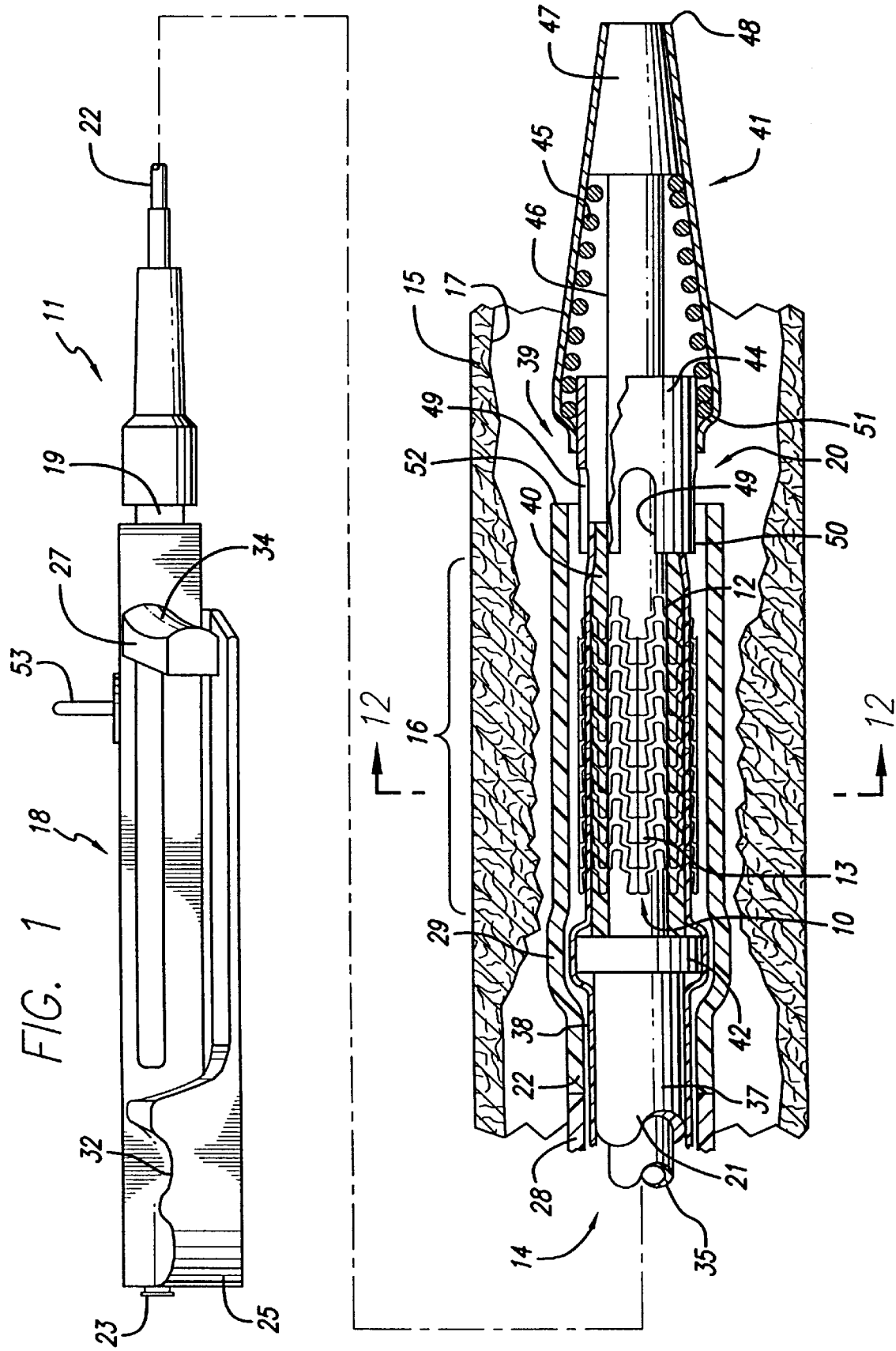
FIG. 1 is an elevational view, partially in section, depicting the self-expanding stent embodying features of the present invention which is mounted on a stent delivery system made in accordance with the present invention and disposed within a vessel.

The stent delivery system 11 has an elongated catheter body 14 for delivering and deploying the compressed stent 10 (as shown in FIG. 1) within an artery 15 or other vessel. The artery 15, as shown in FIGS. 1 and 2, has an area of treatment 16 which has just undergone an angioplasty procedure, or similar procedure, in which atherosclerotic plaque of a stenosis has been compressed against the inside wall 17 of the artery 15 to increase the diameter of the occluded area of artery 15. The expanded stent 10 (shown in FIG. 2) is implanted within the artery 15 to help hold open the artery in this area and to help prevent restenosis.

The stent delivery system 11 includes a housing assembly 18 attached to the proximal end 19 of the delivery catheter 14 which is used to manually deploy the compressed stent 10 mounted on the distal end 20 of the delivery catheter 14 into the diseased artery 15. The delivery catheter 14 includes an inner tubular member 21 which extends within an outer tubular member 22 in a coaxial arrangement. The inner tubular member 21 has a luer fitting 23 attached at its proximal end 24 which is rigidly attached to the base 25 of the housing assembly 18 to prevent the inner member 21 from moving relative to the outer member 22 during stent deployment. The outer member 22 has a proximal end 26 which is attached to a pull-back handle 27 which is designed to move axially (along the longitudinal axis of the delivery catheter 14) within the base 25. At the distal end of the outer tubular member 22 is a flexible restraining sheath 29 which is welded or otherwise attached to the elongated shaft 28 of the outer tubular member 22. This restraining sheath 29 is designed to hold the stent 10 in its compressed or collapsed state and is retracted by moving the pull back handle 27 (in the direction of the arrows 30 shown in FIG. 4) which moves the restraining sheath in a likewise fashion while maintaining the inner tubular member 21 stationary during stent deployment.

Figure 8:
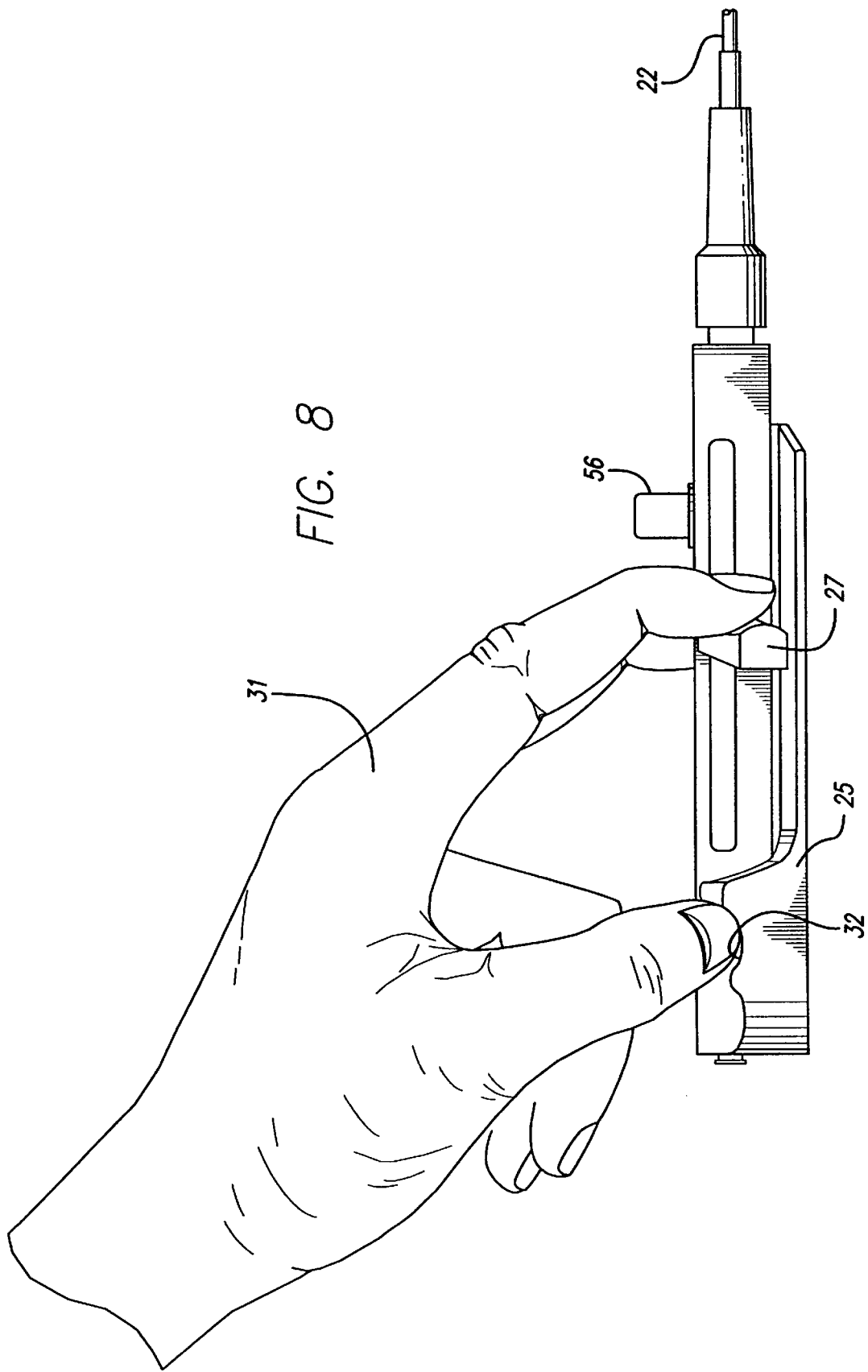
FIG. 8 is an elevational view showing the housing assembly of the present invention being manually operated.

FIG. 8 shows how the pull-back handle 27 of the housing assembly 18 can be grasped by a single hand 31 of the physician to deploy the collapsed stent 10. The housing assembly 18 includes a pair of thumb grooves 32 which are located at the proximal end 33 of the base 25 and are adapted to receive the thumb of the physician when the stent is to be deployed. The pull-back handle 27 includes a pair of recesses 34 adapted for the fingers of the physician. The physician simply pulls back on the pull-back handle 27 to deploy the stent 10 once in proper position. Since the thumb grooves 32 are perpendicular to the axis of the restraining sheath 29, the physician can usually only push downward on the base 25 of the housing assembly 18 and not forward. This helps prevent the housing assembly 18 from moving forward, towards the patient. By directing the force of the physician's hand down on the base and away from the patient via the pull-back handle 27, rather than forward, the distal end of the delivery catheter 14 should be prevented from moving within the artery to insure an accurate placement of the stent 10 in the body lumen. Since the stent delivery system 11 can be used with just one hand, the physician's other hand is free to perform other tasks, such as stabilizing the guiding catheter used during the procedure. Stabilizing the guide catheter enhances deployment accuracy. Details concerning additional features of the housing assembly 18 are provided below.

In one embodiment of the present invention, the inner tubular member 21 is a composite structure formed from three coaxial layers of materials, each material having a specific function. The innermost layer is a guide wire lumen 35 which runs the entire length of the delivery catheter 14. This guide wire lumen 35 can be made from a material such as a high density polyethylene (HDPE) or similar material which provides a low friction interface between the delivery catheter and the guide wire (not shown) which is also used in the procedure to advance the catheter body 14 to the target site using over-the-wire techniques that are well known in the art. For example, the guide wire lumen 35 can be made from tubing which is compatible with a 0.014 inch guide wire for an over-the-wire configuration.

The application of tensile force to the shaft of the outer tubular member 22 and restraining sheath 29 during stent deployment creates an equal and opposite compressive force on the inner tubular member 21. For the restraining sheath 29 to retract (via the movement of the pull-back handle 27) without causing the rest of the delivery catheter 14 to buckle, the inner tubular member 21 must possess sufficient column strength to prevent buckling or deformation. Otherwise, buckling or deformation to the inner tubular 21 can cause the distal end 20 of the delivery catheter 14 to move within the artery, causing inaccurate deployment of the stent. Therefore, the second layer of the inner tubular member may be comprised of tubular elements which possess sufficient rigidity to prevent unwanted buckling or deformation, yet are flexible enough to track along the torturous anatomy to the target site.

In a preferred embodiment of the present invention, the second layer of the inner tubular member 21 includes a proximal portion 36 made from a stainless steel hypotube, or similar material, and a distal portion 37 comprising of more flexible material such as polyethereketone (PEEK) or similar material or a wound coil which possess excellent compressive strength yet is reasonably flexible. The proximal portion 36 is made from stainless steel hypotube which provides maximum strength, but is fairly rigid. However, this is not a concern since this proximal portion 36 of the inner tubular member 21 remains relatively straight within the guiding catheter during the procedure. The distal portion 37, which is approximately 15 centimeters in length, must exit the guiding catheter and track through the torturous anatomy to reach the target site. Therefore, this portion must possess sufficient compressive strength yet be fairly flexible.

The outermost layer of the inner tubular member 21 may be made from a layer of shrink tubing 38 having low frictional characteristics. A suitable material would be linear low density polyethylene (LLDPE). The outer layer of shrink tubing 38 is utilized to reduce the amount of friction created when the outer tubular member 22 is retracted over the length of the inner tubular member 21. The outer surface of the inner tubular member 21 can also be coated with a silicone lubricant such as Microglide manufactured by Advanced Cardiovascular Systems, Inc., Santa Clara, Calif., to further reduce the amount of frictional buildup between the outer tubular member 22 and inner tubular member 21.

A luer fitting 23 attached to the proximal portion 36 of the inner tubular member 21 is rigidly mounted to the base 25 of the housing assembly 18 to permanently secure the inner member to the housing assembly. The luer fitting 23 can be attached to the inner tubular member 21 by trimming the guide wire lumen 35 at the proximal end and then gluing the fitting 23 and proximal portion 36 together with a suitable adhesive. It should be appreciated that the mounting of the inner tubular member to the housing assembly 18 can be achieved in any number of ways without departing from the spirit and scope of the present invention.

The distal end 39 of the inner tubular member 21 includes a stent holder 40 upon which the compressed stent 10 is mounted. A tip assembly 41 having a tapered configuration is located at the distal end of the delivery catheter 14 to help cross an occluded area in the diseased artery. A tantalum marker 42 is attached to the proximal end of the stent holder 40 by adhesive or other means. The tantalum marker 42 is radiopaque and is used to locate the proximal end of the stent 10. In addition, the marker 42 is larger than the inner diameter of the compressed stent 10 to provide an abutting surface for the stent 10 to push against when the restraining sheath 29 is being retracted. The stent holder 40 can be made from a piece of tubing which correctly sizes the mismatch between the inner diameter of the collapsed stent 10 and the rest of the inner tubular member 21. For example, the stent holder can be made from a composite material having a mix of 75% LLDPE which makes it soft and flexible with 25% HDPE to improve process ability. The stent holder 40 has a tapered distal tip 43 to facilitate attachment to the tip assembly 41. The stent holder 40 can be glued directly onto the guide wire lumen 35 and is encased under the layer of shrink tubing 38 which forms the outermost layer of the inner tubular member 21.

The tip assembly 41 is made from a tubular element 44 made from a small segment of stainless steel hypotube which has a tapered wound coil 45 welded to the distal end of the tubular element 44. The coil 45 and the distal portion of the mounting segment are incased in molded urethane to form the tip component 46. A radiopaque tungsten element 47 is placed at the distal end of the tip component 46. The guide wire lumen 35 extends through the tip component to the distal tip 48. An opening (not shown) at the distal end of the assembly tip 41 permits the guide wire to advance therethrough to allow the delivery catheter 14 to track along the wire into the diseased artery.

The tubular element 44 has a number of circumferential slots 49 cut into the proximal end of the element 44. The slots 49 provide a channel which allows fluid to escape when the device is being flushed to evacuate air from the delivery system. The proximal end 50 of the tubular element 44 abuts the distal end of the stent holder 48 and is partially covered by the restraining sheath 29. At least a small segment of the slots 49 should be unsheathed to allow the flushing fluid and air to escape from the system during the air evacuation step. The tip component 46 includes a shoulder 51 which is raised from the outer surface of the tubular element 44 so that the distal end 52 of the restraining sheath 29 remain flush with the tip component 46. This particular configuration prevents the distal end 52 of the restraining sheath 29 from being exposed while the delivery catheter is being maneuvered through the curves of the anatomy.

The elongated shaft 28 of the outer tubular member 22 can be made from a material such as cross-linked HDPE. The restraining sheath 29 can be made from a material such as polyolefin which is welded or otherwise attached to the shaft 28 of the outer tubular member. A material such as polyolefin is used since it has sufficient strength to hold the compressed stent and has relatively low frictional characteristics to minimize any friction between the stent 10 and the sheath 29. Friction can be further reduced by applying a coat of silicone lubricant, such as Microglide, to the inside surface of the restraining sheath 29 before the stent 10 is loaded onto the stent holder 40.

Figure 5:
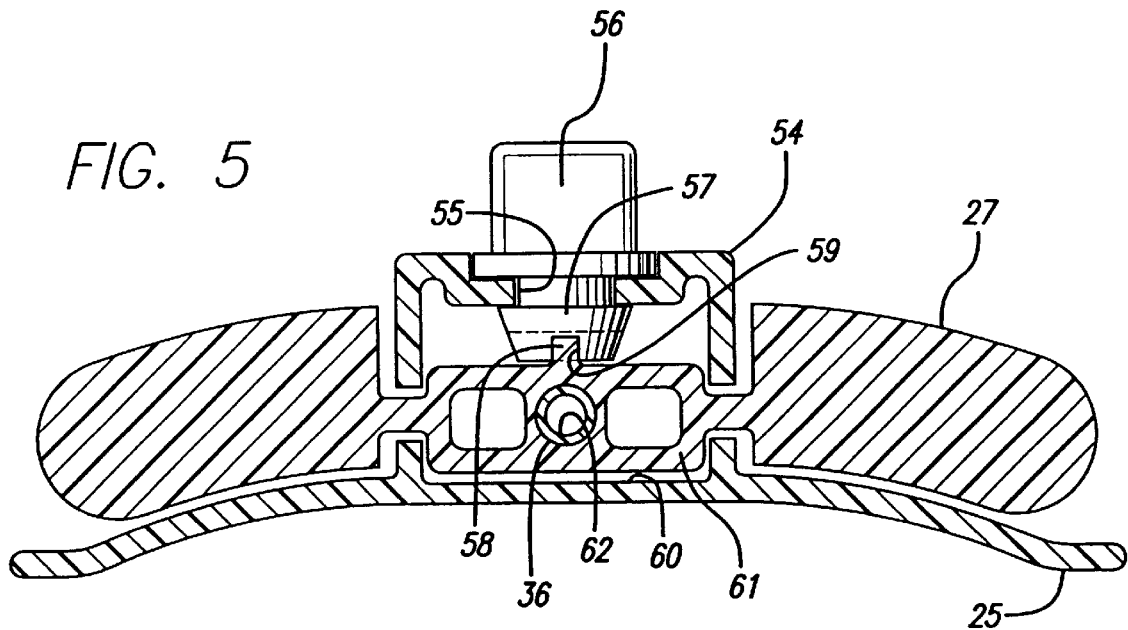
FIG. 5 is a cross-sectional view of the housing assembly taken along lines 5—5.
Figure 6:
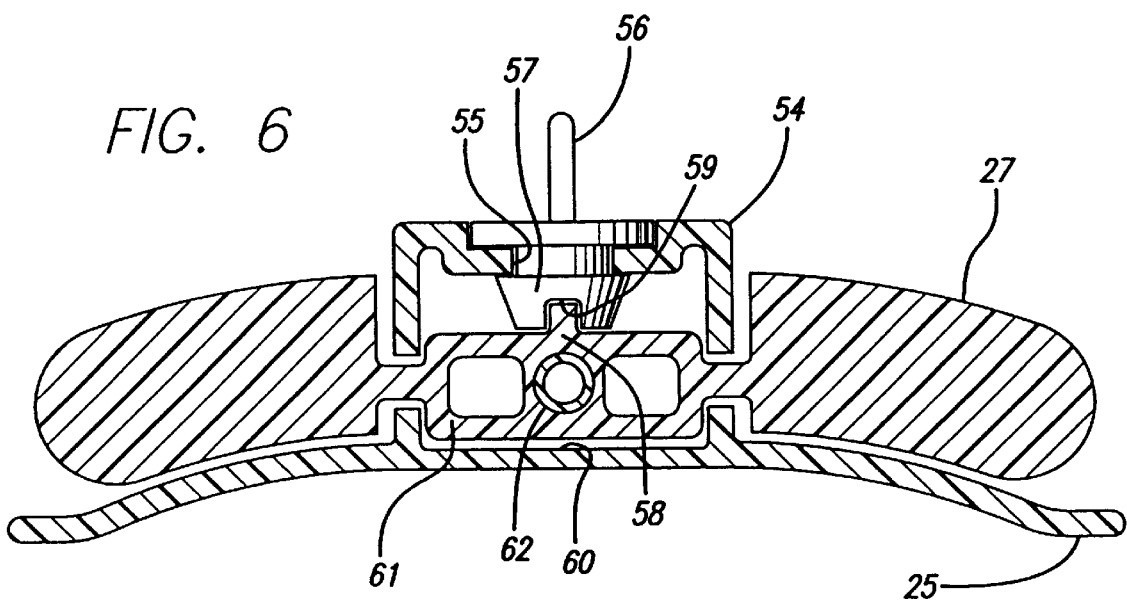
FIG. 6 is a cross-sectional view of the housing assembly taking along lines 6—6.

Referring now to FIGS. 3–6, the housing assembly 18 is shown including a lock mechanism 53 which is designed to maintain the pull-back handle 27 in its forward position until the stent is ready to be deployed. The base includes a cover 54 which extends from the distal end of the base 25 to its proximal end. This cover 54 includes an opening 55 for receiving the lock mechanism 53. The lock mechanism 53 is operated by simply grasping the control knob 56 and rotating it to either the locked or unlocked position. FIGS. 3 and 5 show the lock mechanism 53 in the locked position. In the locked position, a shoulder portion 57 of the lock mechanism 53 comes in contact with a raised projection 58 formed on the pull-back handle 27. The shoulder portion 57 includes a slotted opening 59 through which the raised projection 58 slides when the pull-back handle 27 is retracted to deploy the stent. The shoulder portion 57 abuts the raised projection 58 preventing it from moving passed it since the slotted opening 59 is oriented 90° out of phase with the raised protection 58. Referring now to FIGS. 4 and 6, which show the lock mechanism in the unlocked position, the slotted opening 59 on the shoulder 57 is now aligned with the raised projection 58 to allow it to pass therethrough. In the open position shown in FIGS. 4 and 6, the lock mechanism 53 allows the pull-back handle 27 to be pulled back in the direction of the arrow 30, which retracts the restraining sheath to deploy the compressed stent.

The base 25 of the housing assembly 18 includes a slotted channel 60 which is adapted to receive the central section 61 of the pull-back handle 27. The central portion 61 includes an opening 62 through which the proximal portion 36 of the inner tubular member 21 extends to a location where the luer fitting 23 is rigidly mounted in a recess (not shown) or similar mounting element on the base 25. The proximal end 26 of the outer tubular member 22 is affixed to the front plate 63 of the pull-back handle 27 so that as the pull-back handle is retracted, the outer member 22 and restraining sheath 29 are likewise retracted, accordingly while the inner member 21 remains stationary.

As can be seen in FIGS. 5 and 6, the base 25 has an unique contour which increases the surface area of the base and is contoured to fit the patient's leg. Thus, during the procedure, the physician can place the housing assembly 18 directly onto the leg of the patient where it should remain stationary as the sheath is being retracted. The unique design of the housing assembly permits the physician to use just one hand to retract the pull-back handle 27 to deploy the compressed stent into its expanded condition without the worry of possibly moving the delivery catheter during the deployment process.

The stent delivery system of the present invention also includes a unique flushing system which is used to evacuate air from the system. It is important to evacuate air from the system when the stent delivery system is being used to place a stent in the carotid artery since it is undesirable to have even a small air bubble enter the arteries in the brain. In other instances, it may be desirable to have a fluid preplaced into the system to prevent the possible accumulation of blood between the retractable sheath and the inner tubular member since stagnated blood has the tendency to coagulate and cause thrombosis. For these reasons, it may be beneficial to pre-flush the system before placing the delivery catheter in the patient.

Figure 12:
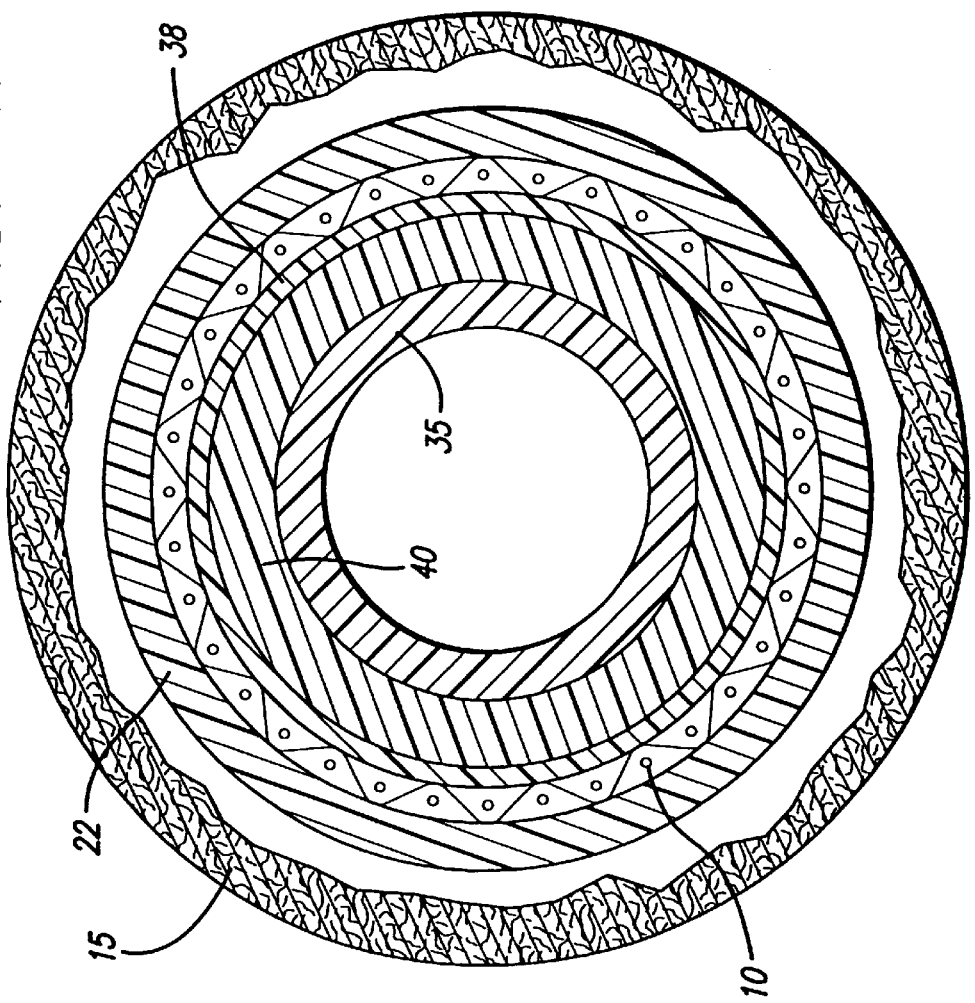
FIG. 12 is a cross-sectional view of the catheter body shown in FIG. 1 taken along lines 12—12.
Figure 11:
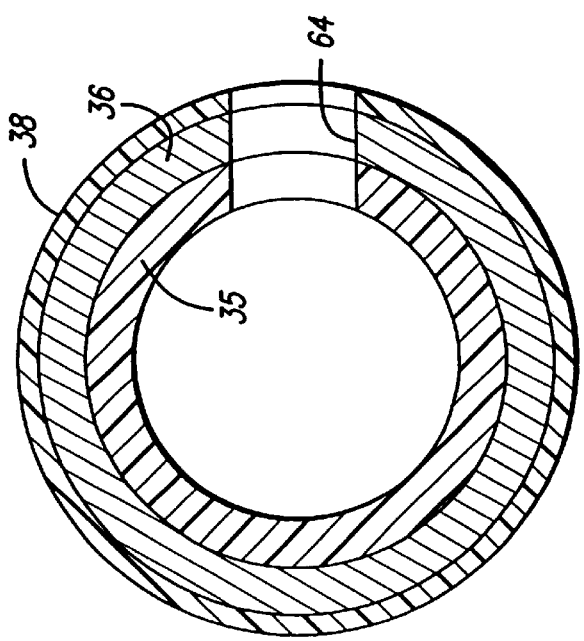
FIG. 11 is a cross-sectional view of the inner tubular member taken along lines 11—11.

Referring now to FIGS. 7, 11 and 12, the flushing system consists of openings 64 extending through the inner tubular member 21 in the area of where the proximal portion meets the distal portion of the inner member (FIG. 7). The openings 64 are drilled through to the guide wire lumen 35 to effectively open up a passageway from the guide wire lumen 35 to the annular space formed between the inner tubular member 21 and the outer tubular member 22. A syringe is attached to the luer fitting 23 of the housing assembly 18 and sterile fluid is pumped into the guide wire lumen 35 in order to flush air from the system. A mandrel (not shown) placed in the guide wire lumen 35 at the tip assembly 41 blocks the flow of the sterile fluid through the distal tip. The sterile fluid is thus forced to flow out of the small openings 64 into the annular space formed between the inner tubular member and outer tubular member. The fluid eventually flows past the collapsed stent (FIG. 12) where the fluid and any air in the system will escape through the small circumferential slots 49 cut into the tubular element 44 of the tip assembly 41. Once fluid is observed dripping from the distal end 52 of the restraining sheath 29, the mandrel is removed since air has been evacuated from the system. Since the gap sizes are so small between the various components, capillary force prevents air from infiltrating the delivery system once the evacuation has been completed.

Referring now to FIGS. 9 and 10, a preferred embodiment of the stent 10 of the present invention is shown. As can be seen in FIG. 10, the cylindrical element 12 of stent 10 illustrates the serpentine pattern having a plurality of peaks and valleys which aid in the even distribution of expansion forces. In this embodiment, the interconnecting members 13 serve to connect adjacent valleys of each adjacent cylindrical element 12 as described above. The various peaks and valleys generally have U, W and (inverted U) shapes, in a repeating pattern to form the cylindrical element 12. During expansion, doubled curved portions (W) 70 located in the region of the valley where interconnecting members 13 are connected, have the most mass and are the stiffest structure during deformation, while peak portions (inverted U) 72 are the least stiff, and valley portions (U) 74 have an intermediate stiffness. In the embodiment shown in FIGS. 9 and 10, there are three repeating patterns of peaks and valleys in each cylindrical element 12, which allows the stent to be collapsed to a very small profile. Each peak portion (inverted U) 72 has a shoulder portion 75 which has a different radius of curvature than the radius of curvature for the valley portions (U 74) and peak portion (inverted U) 72. This shoulder region 75 provides a transition region between the peak portion (inverted U) 72 and the valley portions (U) 74 and double curved portion (W) 70 to allow adjacent cylindrical elements to overlap and thereby better support the artery walls with smaller gaps between stent struts. In this manner, the shoulder portion 75 provides more dense coverage of the serpentine pattern of the cylindrical element to create a fairly uniform strut pattern which fully supports the walls of the diseased artery. For this reason, there are no or few areas of the stent wall which do not have struts for supporting the walls of the artery.

Each interconnecting member 13 is aligned collinearly with each other to form a substantially continuous spine 76 which extends along the length of the stent 10. This continuous spine 76 prevents the stent from shortening longitudinally when the cylindrical elements 12 are expanded radially. The spine 76 also helps prevent the stent from storing energy as the restraining sheath 29 is retracted over the stent during deployment. As a result, the stent 10 will not "jump" off the stent holder 40 as the stent rings 12 are released by the restraining sheath 29. Therefore, more accurate deployment of the stent can be achieved. The number and location of the interconnecting members 13 can be varied in order to develop the desired longitudinal flexibility in the stent structure both in the compressed condition as well as the expanded condition. The interconnecting members do not provide flexibility per se, but their location and frequency can enhance the flexibility derived from the cylindrical elements. Generally, the greater the longitudinal flexibility of the stent, the easier and more safely it can be delivered to the target site, especially where the implantation site is on a curved section of the body lumen, such as a coronary artery or a peripheral blood vessel. The number of spines 76 formed by the collinear arrangement of interconnecting elements 13 can vary from one to as many as can be reasonably placed on a stent, however, for a minimal energy storage with a maximum flexibility, two to four spines are recommended.

As shown in FIG. 2, stent 10 serves to hold open artery 15 after the catheter body 14 is withdrawn from the artery and help reduce the likelihood of restenosis. Due to formation of stent 10 from an elongated tubular member, the undulating component of the cylindrical elements 12 of stent 10 is relatively flat in transverse cross-section, so that when the stent is expanded, the cylindrical elements 12 are pressed into the wall of the artery 15 and do not result in an interference with the blood flow through the artery 15. Cylindrical elements 12 which are pressed into the wall of artery 15 will eventually be covered with endothelial cell growth which further minimizes blood flow turbulence. The serpentine pattern of cylindrical sections 12 provide good packing characteristics to prevent stent movement within the artery. Moreover, the closely spaced cylindrical elements 12 at regular intervals provide uniform support for the wall of artery 15. While FIGS. 1 and 2 depict a vessel having an area of compressed plaque, the stent 10 can be used for purposes such as repairing a detached lining in the artery, or to assist in attaching a vascular grasp (not shown) when repairing an aortic abdominal aneurysm.

Figure 13:
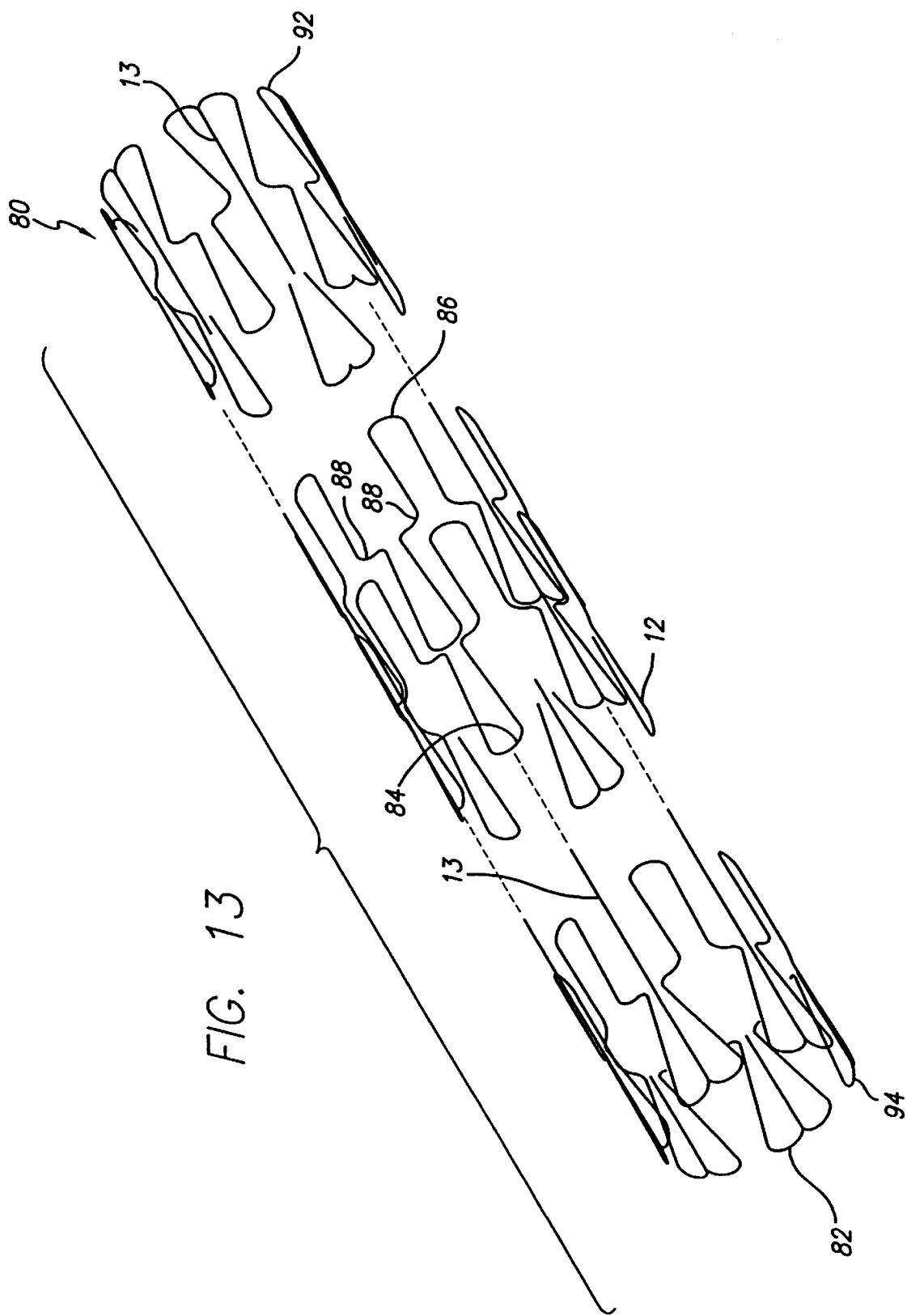
FIG. 13 is a perspective of an alternative embodiment of the stent embodying features of the present invention in an unexpanded position.

Another embodiment of a stent 80 made in accordance with the present invention is disclosed in FIGS. 13–17. FIG. 13 is an enlarged perspective view of a stent 80 having a number of interconnecting elements 13 between adjacent radially expandable cylindrical elements 12. As can be seen in both FIGS. 14 and 15, the cylindrical element 12 of stent 80 has a serpentine pattern having a plurality of peaks and valleys which aid in the even distribution of expansion forces. In this embodiment, as with the previously described embodiment, the various peaks and valleys generally have U, W and inverted U-shapes in a repeat pattern to form the cylindrical element 12. During expansion, double-curved portions (W) 82, located in the region of the valley where interconnecting members 13 are connected, have the most mass and are the stiffest structure during deployment. Valley portions (U) 84 have an intermediate stiffness. The peak portions (inverted U) 86 are the least stiff. A shoulder portion 88 which has a different radius of curvature than the radius of curvature for the valley portions and peak portion is located between each peak portion (inverted U) 86 and the respective valley portion (U) 84 or double-curved portion (W) 82. This shoulder region 88, like the shoulder region 75 shown in the previous embodiment of the stent 10, provides a transition region between the peak portions and the valley portions to allow adjacent cylindrical elements to overlap and therefore better support the arterial walls with smaller gaps between stent struts.

The double-curved portions (W) 82 is somewhat similar to the double-curved portion (W) 70 described in the previous embodiment, except that the double-curved portion (W) 82 has a slight inward angulation. Likewise, the peak portion (inverted U) 86 and valley portion (U) 84 also have a more inward angulation than their counterparts shown in FIGS. 9 and 10. This inward angulation of the (U), (W) and (inverted U) portions allow each of the cylindrical elements 12 to collapse closer to each other, resulting in a smaller collapsed diameter.

FIGS. 16 and 17 show how the (U) and (W) portions have a inward angulation, where the arc angle of the radius "wraps" more than 180 degrees. FIGS. 16 and 17 shows a line A which denotes the longitudinally axis of the stent 80. Line B denotes the angle at which the legs of the U's and W's invert inward to allow a cylindrical element to be aligned closer to an adjacent cylindrical element. Hence, the stent can be collapsed to a smaller diameter without having to resort to a narrower strut width. Additionally, the cell height (indicated by arrow 90 in FIG. 15) can be longer to enable a larger expansion size without exceeding the material's strain limits. This allows the embodiment of the stent 80 shown in FIGS. 13–15 to expand to a larger maximum size (up to about 10 mm) while allowing the same device to be collapsed to a smaller size, down to about 0.069 inches, rather than about 0.073 inches.

The stent 80 further includes end rings 92 and 94 which include double-curved portions (W) 82 at the outermost edge to increase the strength of the stent 80 at its ends.

Additional interconnecting members 13 are utilized in this particular design to further increase the axial strength of the ends of the stent 80. As can be seen in FIG. 14, each of the double-curved portions (W) 82 of the end rings 92 and 94 have an interconnecting member 13 which attaches to the respective adjacent cylindrical element 12. This allows for greater strength at the ends of the stent where it may be needed to prevent the stent from deploying into a "cigar" shape once implanted in the patient's vasculature. The end rings 92 and 94 also increase the amount of material at the ends of the stent which may increase radiopacity as well. As result, the physician may have an easier time in visualizing the location of the stent 80 both on the delivery catheter and once the stent is implanted within the patient's vasculature.

Stents of various lengths can be made by adding or subtracting cylindrical elements between the end rings 92 and 94 of the stent 80. For example, the stent 80 can be made in sizes of 20 mm, 30 mm and 40 mm, but could also be made as small as 9 mm to as large as about 200 mm, depending upon the application to which the stent will be utilized. The stent 80 also includes a number of continuous spines 76 which extend along the length of the stent 80 to help prevent the stent from shortening longitudinally when the cylindrical elements 12 are expanded radially. As with the previously described embodiments shown in FIGS. 9 and 10, the spines 76 also help prevent stents from storing energy as the restraining sheath is retracted over the stent during deployment. As a result, the stent 80 should not "jump" off the stent holder as the cylindrical elements are released by the restraining sheath. Therefore, more accurate deployment of the stent can be achieved. The number of spines 76 formed by the collinear arrangements of interconnecting members 13 can vary from one to as many as can be reasonably placed on the stent, however, for a minimum energy storage with maximum flexibility, again, two to four spines are recommended.

Referring now to FIG. 18, an alternative tip assembly 100 for the delivery system 11 is shown. It should be noted that where like elements have already been described in conjunction with the stent delivery system 11 disclosed in FIGS. 1–8, similar reference numbers are used herein. The modifications of tip assembly 100 include the elimination of the tubular element 44 which provided a conduit to the tip for evacuating air from the delivery system. Additionally, the tip assembly eliminates need for a round coil 45 and the radiopaque tungsten element 47 which was placed at the distal end of the tip component 46. As a result, the tip assembly 100 may be less costly to manufacture and easier to place on the stent holder 40.

Referring again to FIG. 18, a tip component 102 is shown bonded directly to the stent holder 40. This tip component 102 can be made from material such as poly-ether-block-amide sold under the name of PEBAX, or other similar polymeric material or alloy suitable for use. A highly radiopaque material, such as $BaSO_4$, could be compounded with the PEBAX, or any other polymeric material used to form the tip component 102, to increase the radiopacity of the tip component 102. A marker band 104, which is located on the stent holder 40 distal to the expandable stent 80, provides the physician with an additional marker for determining the location of the stent when placing it within the patient's vasculature. The stent holder 40 is shown extending approximately halfway into the lumen 106 of the tip component 102 to provide a sufficient area for bonding purposes. Adhesives are used to bond the tip component to the portion of the stent holder 40 which extends into the lumen 106. The guide wire lumen 35 also extends into the lumen 106 of the tip component 102 to allow the guide wire (not shown) to extend through the distal opening 108 of the tip component 102. The tip component 102 includes a recessed area 99 over which the restraining sheath extends once the stent is mounted on the stent holder 40. A rounded proximal edge 101 formed on the tip component 102 provides a smooth edge and reduces the possibilities of the tip component 102 catching on a deployed stent when the delivery system is being removed from the patient.

In an alternative method of attaching the tip component 102 to the stent holder 40, the end of the stent holder 40 does not have to extend into the lumen 106 of the tip component 102, but rather, can terminate proximal to the opening 110 of the component 102. The guide wire lumen 35 would thus extend into the lumen 106 of the tip component 102. Adhesive could be applied to the guide wire lumen 35 directly to adhesively bond the tip component 102 thereto. It should be appreciated that still other methods of attaching the tip component 102 to the stent holder can be employed without departing from the spirit and scope of the present invention.

Additional minor modifications to the catheter system could be made such as placing the marker band 42 over the layer of shrink tubing 38 as is shown in FIG. 18, rather than have the layer of shrink tubing 38 encapsulate the marker 42 as is shown in FIGS. 1 and 2. The proximal end of the inner tubular member 21 can be further stiffened by placing an inner hypotube inside the existing guide wire lumen 35. In this manner, the shaft of the inner tubular member 21 can be reinforced to resist buckling. Additionally, the luer fitting 23 on the housing assembly 18 can be increased in size to allow for guide wire exchanges.

The elimination of the tubular member 44 utilized in the flushing system in this particular embodiment does not sacrifice the ability of the tip assembly 100 to evacuate trapped air from the catheter system. A similar method of evacuating air from the system, as previously described and shown in FIGS. 7, 11 and 12, can be used. For example, a syringe can be attached to the luer fitting 23 of the housing assembly 18 to pump sterile fluid into the guide wire lumen 35 to flush air from the system. Again, a mandrel or stylet (now shown) is placed in the guide wire lumen at the distal opening 108 to block the flow of sterile fluid. Any trapped air will be forced to escape through the distal end of the restraining sheath 29 or through the distal opening 108 on the tip component 102. Once fluid is observed dripping from the distal end of the retraining sheath and the distal opening 108, the mandrel can be removed since air has been evacuated from the system. Since the gap sizes are so small between the various components, capillary force prevents air from infiltrating the delivery system once evacuation has been completed.

The stent of the present invention can be made in many ways. However, the preferred method of making the stent is to use the well-known process of laser cutting to cut a thin-walled tubular member, to remove portions of the tubing in the desired pattern for the stent, leaving relatively untouched the portions of the metallic tubing which are to form the stent. It is preferred to cut the tubing in the desired pattern by means of a machine-controlled laser.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. No. 5,759,192 (Saunders) and U.S. Pat. No. 5,780,807 (Saunders), which have been assigned to Advanced Cardiovascular Systems, Inc. and are incorporated herein by reference in their entirety.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machinecontrolled laser as described. The entire space between collets can be patterned using the $CO_2$, Nd or YAG laser set-up of the foregoing example. The program for control of the apparatus is dependent on the particular configuration used and the pattern to be ablated in the coding.

A suitable composition of Nitinol used in the manufacture of the stent of the present invention is approximately 55% nickel and 45% titanium (by weight) with trace amounts of other elements making up about 0.5% of the composition. The austenite transformation temperature is between about −15° C. and 0° C. in order to achieve superlastecity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of Nitinol can be utilized, as can other self-expanding alloys, to obtain the same features of a self-expanding stent made in accordance with the present invention.

The stent of the present invention can be laser cut from a tube of super- elastic (sometimes called pseudo-elastic) nickel titanium (Nitinol) whose transformation temperature is below body temperature. The stent diameters can cut with the same stent pattern, and the stent is expanded and heat treated to be stable at the desired final diameter. The heat treatment also controls the transformation temperature of the Nitinol such that the stent is super elastic at body temperature. The transformation temperature is at or below body temperature so that the stent is superelastic at body temperature. The stent is electro polished to obtain a smooth finish with a thin layer of titanium oxide placed on the surface. The stent is usually implanted into the target vessel which is smaller than the stent diameter so that the stent applies a force to the vessel wall to keep it open.

The stent tubing may be made of suitable biocompatible material besides super-elastic nickel-titanium (NiTi) alloys. In this case the stent would be formed full size but deformed (e.g. compressed) into the restraining sheath of the delivery catheter to facilitate intraluminal delivery to a desired intraluminal site. In the compressed state, a portion of the stent material is in the martensite phase, and upon release of the restraining sheath when the stent reaches the desired intraluminal location, the stent expands due to the transformation back to the more stable austenite phase. Further details of how NiTi super-elastic alloys operate can be found in U.S. Pat. No. 4,665,906 (Jervis) and U.S. Pat. No. 5,067,957 (Jervis).

The stent diameters are very small, so the tubing from which it is made must necessarily also have a small diameter. For PTCA applications, typically the stent has an outer diameter on the order of about 1.65 mm (0.065 inches) in the unexpanded condition, the same outer diameter of the hypotube from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. This stent is also designed for carotid applications, so the outer diameter of the tubing would typically be about 0.095 inches with a wall thickness of about 0.007 inches. The diameters of a carotid stent typically would be about 5–10 mm. While it is preferred that the stents be made from laser cut tubing, those skilled in the art will realize that the stent can be laser cut from a flat sheet and then rolled up in a cylindrical configuration with the longitudinal edges welded to form a cylindrical member.

While the invention has been illustrated and described herein in terms of its use as intravascular stents, it will be apparent to those skilled in the art that the stents can be used in other instances in all conduits in the body, such as, but not limited to, the urethra and esophagus. Since the stent of the present invention has the novel feature of self-expanding to a large diameter while retaining its structural integrity, it is particularly well suited for implantation in almost any vessel where such devices are used. This feature, coupled with limited longitudinal contraction of the stent when it is radially expanded, provide a highly desirable support member for all vessels in the body. Other modifications and improvements may be made without departing from the scope of the invention.

What is claimed is:

1. A self-expanding stent having longitudinal flexibility for implanting in a body lumen and being expandable from a compressed condition to an expanded condition, comprising:

a plurality of adjacent cylindrical elements made from a self-expanding material, each cylindrical element having a circumference extending around a longitudinal stent axis and being substantially independently expandable in the radial direction, wherein the plurality of adjacent cylindrical elements are arranged in alignment along the longitudinal stent axis and form a generally tubular member, the cylindrical elements are formed in a generally serpentine wave pattern and contain alternating valley portions and peak portions with a space formed between each valley and peak portion, the peak portions of the cylindrical element are adapted to extend within the spaces formed on an adjacent cylindrical element, and the cylindrical elements at each end of the stent have a plurality of double curved portions forming the outermost edge of the stent; and a plurality of interconnecting members extending between the adjacent cylindrical elements and connecting the adjacent cylindrical elements to one another, wherein some of the interconnecting members are aligned collinearly with respect to each other to form a continuous spine which extends along the length of the stent.

2. The stent of claim 1, wherein the interconnecting members are connected at the double curved portions of each cylindrical element.

3. The stent of claim 1, wherein the plurality of interconnecting members form a plurality of continuous spines which extend along the length of the stent.

4. The stent of claim 1, wherein a plurality of interconnecting members attach each of the end cylindrical elements to an adjacent cylindrical element.

5. The stent of claim 1, wherein said stent is formed of a biocompatible material such as nickel titanium alloy.

6. The stent of claim 1, wherein the stent is formed from a single piece of tubing.

7. The stent of claim 1, wherein the valley portions include U-shaped portions and W-shaped portions and the peak portions include inverted U-shaped portions.

8. The stent of claim 7, wherein the U-shaped and inverted U-shaped portions have legs defining the shape of the respective portion with the legs of each U-shaped and inverted U-shaped portion being inverted slightly inward to each other when in the compressed condition.

9. The stent of claim 7, wherein the W-shaped portions have outer legs defining the shape of the respective portion with the outer legs of each W-shaped portion being inverted slightly inward to each other when in the compressed condition.

10. A flexible intravascular stent for implanting in a body lumen, comprising:

a plurality of cylindrical elements interconnected to form the stent, each cylindrical element arranged in alignment along a longitudinal stent axis and having a first delivery diameter and a second implanted diameter;

each cylindrical element being formed in a generally serpentine wave pattern having a plurality of alternating valley portions and peak portions with a space formed between each alternating valley portion and peak portion, wherein peak portions of the cylindrical elements are adapted to extend within the spaces formed on an adjacent cylindrical element and the cylindrical elements at each end of the stent have a multiplicity of double curved portions which form the outermost edge of the stent; and a plurality of interconnecting members extending between the adjacent cylindrical elements and connecting the adjacent cylindrical elements to one another, wherein some of the interconnecting members are aligned collinearly with respect to each other to form a continuous spine which extends along the length of the stent; and a plurality of interconnecting members extending between the adjacent cylindrical elements and connecting the adjacent cylindrical elements to one another, wherein some of the interconnecting members are aligned collinearly with respect to each other to form a continuous spine which extends along the length of the stent.

11. The intravascular stent of claim 10, wherein:

a shoulder region extends between each of the alternating valley portions and peak portions.

12. The intravascular stent of claim 11, wherein:

the shoulder regions increase the width of the space formed between alternating valley portions and peak portions.

13. The intravascular stent of claim 10, wherein:

each cylindrical element includes a shoulder region which extends between each alternating peak portion and valley portion.

14. The intravascular stent of claim 13, wherein:

each shoulder region increases the width of the space formed between alternating peak portions and valley portions.

15. The intravascular stent of claim 14, wherein:

each peak portion is adapted to fit within the spaces formed between alternating peak portions and valley portions of an adjacent cylindrical element.

16. The intravascular stent of claim 15, wherein:

the stent is made from a biocompatible material which is self-expanding.

17. The intravascular stent of claim 10, wherein:

each peak portion of a cylindrical element is aligned to fit within the space formed between the alternating valley portions and peak portions of an adjacent cylindrical element.

18. The intravascular stent of claim 17, wherein:

each peak portion of a cylindrical element is aligned in phase with a peak portion of an adjacent cylindrical element.

19. The intravascular stent of claim 10, wherein:

at least one of the valley portions of each cylindrical element is a double-curved portion.

20. The intravascular stent of claim 19, wherein:

a plurality of interconnecting members extends from the double-curved portions of the cylindrical elements to connect adjacent cylindrical elements together.

21. The intravascular stent of claim 10, wherein:

the stent is made from a biocompatible material which is self-expanding.

22. The intravascular stent of claim 10, wherein:

valley portions include U-shaped portions and W-shaped portions and the peak portions include U-shaped portions, the U-shaped and inverted U-shaped portions have legs defining the shape of the respective portion with the legs of each U-shaped and inverted U-shaped portion being inverted slightly inward to each other when placed in the first delivery diameter.

23. The stent of claim 22, wherein the W-shaped portions have outer legs defining the shape of the respective portion with the outer legs of each W-shaped portion being inverted slightly inward to each other when placed in the first delivery diameter.

* * * * *

UNITED STATES PATENT AND TRADEMARK OFFICE
CERTIFICATE OF CORRECTION

PATENT NO.   : 6,709,454 B1
DATED        : March 23, 2004
INVENTOR(S)  : Daniel L. Cox and William James Harrison It is certified that error appears in the above-identified patent and that said Letters Patent is hereby corrected as shown below:

Column 8,
Lines 39 through 40, delete "peripheral arteries such as the carotid artery, and veins." and insert -- such as the carotid artery, peripheral arteries and veins --.

Column 19,
Delete lines 38 through 44, (first duplicative paragraph).

Signed and Sealed this

Twenty-first Day of September, 2004

JON W. DUDAS
*Director of the United States Patent and Trademark Office*